US012758624B2

(12) United States Patent
Wang et al.

(10) Patent No.: US 12,758,624 B2
(45) Date of Patent: Oct. 13, 2026

(54) **INDUSTRIAL PRODUCTION METHOD FOR *STAPHYLOCOCCUS AUREUS* VACCINE**

(71) Applicant: WESTVAC BIOPHARMA CO., LTD., Chengdu (CN)

(72) Inventors: Zhenling Wang, Chengdu (CN); Yuquan Wei, Chengdu (CN)

(73) Assignee: WESTVAC BIOPHARMA CO., LTD., Chengdu (CN)

( * ) Notice: Subject to any disclaimer, the term of this patent is extended or adjusted under 35 U.S.C. 154(b) by 604 days.

(21) Appl. No.: 18/269,978

(22) PCT Filed: Feb. 25, 2022

(86) PCT No.: PCT/CN2022/077827
§ 371 (c)(1),
(2) Date: Jan. 12, 2024

(87) PCT Pub. No.: WO2022/199317
PCT Pub. Date: Sep. 29, 2022

(65) Prior Publication Data

US 2024/0424076 A1 Dec. 26, 2024

(30) Foreign Application Priority Data

Mar. 23, 2021 (CN) ......................... 202110306892.8

(51) Int. Cl.

| | |
|---|---|
| ***A61K 39/085*** | (2006.01) |
| ***A61K 39/00*** | (2006.01) |
| ***A61K 41/00*** | (2020.01) |
| ***A61P 37/04*** | (2006.01) |
| ***C12N 1/20*** | (2026.01) |
| ***C12N 1/36*** | (2006.01) |

(52) U.S. Cl.
CPC ............ *A61K 39/085* (2013.01); *A61P 37/04* (2018.01); *C12N 1/20* (2013.01); *C12N 1/36* (2013.01); *A61K 2039/54* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 4,748,020 | A | 5/1988 | von Malsen-Ponickau |
| 5,770,208 | A | 6/1998 | Fattom et al. |

FOREIGN PATENT DOCUMENTS

| | | | |
|---|---|---|---|
| CN | 103705914 | A | 4/2014 |
| CN | 104189898 | A | 12/2014 |
| CN | 105833259 | A | 8/2016 |
| CN | 110343633 | A | 10/2019 |
| CN | 112402601 | A | 2/2021 |
| CN | 112410239 | A | 2/2021 |
| WO | 2020139308 | A1 | 7/2020 |

OTHER PUBLICATIONS

International Search Report with mailing date of Apr. 1, 2022 for International Application No. PCT/CN2022/077827.
Written Opinion of International Searching Authority with a completion date Mar. 28, 2022 for International Application No. PCT/CN2022/077827.
Diemen, P. M. V. et al. "Irradiated wild-type and Spa mutant *Staphylococcus aureus* induce anti-*S. aureus* immune responses in mice which do not protect against subsequent intravenous challenge" Pathogens and Disease, vol. 68, No. 1, Apr. 16, 2013 (Apr. 16, 2013), pp. 20-26 (see abstract, materials, and method).
First Chinese Office Action with Search Report issued on Dec. 18, 2023 for Chinese Application No. 202110306892.8.
Inas M. Gamal et al., "Assessment of irradiated *Staphylococcus aureus* isolated as a vaccine", Benha Veterinary Medical Journal, vol. 35, Second Edition, pp. 12-30, Dec. 2018.
Pauline M. van Diemen et al, "Irradiated wild-type and Spa mutant *Staphylococcus aureus* induced anti-*S, aureus* immune responses in mice which do not protect against subsequent intravenous challenge", Pathogens and Disease, Apr. 14, 2013 (Apr. 16, 2013), vol. 68 ISSN 2049-632X, 68, pp. 20-26.
International Preliminary Report on Patentability issued on Sep. 12, 2023 for International Application No. PCT/CN2022/077827.

*Primary Examiner* — S. Devi
(74) *Attorney, Agent, or Firm* — JCIP; Joseph G. Chu

(57) ABSTRACT

The present invention belongs to the field of biomedicine, and particularly relates to an industrial production method for a *Staphylococcus aureus* vaccine. The method provided by the present invention ensures industrial production of a vaccine comprising multiple immunogenic components such as whole-cell *Staphylococcus aureus* with stable and controllable quality. The vaccine prepared by the present invention has good immunogenicity, not only an actual inoculated dose is low, but also the vaccine can prevent multiple infectious diseases caused by drug-resistant *Staphylococcus aureus*.

4 Claims, 3 Drawing Sheets

INDUSTRIAL PRODUCTION METHOD FOR *STAPHYLOCOCCUS AUREUS* VACCINE

TECHNICAL FIELD

The present invention belongs to the field of biomedicine, and particularly relates to an industrial production method for a *Staphylococcus aureus* vaccine.

BACKGROUND

*Staphylococcus aureus* is an important conditioned pathogen. In the adult population, about 20% of people carry *Staphylococcus aureus* continuously, and another 30% carry *Staphylococcus aureus* intermittently. *Staphylococcus aureus* may cause skin and soft tissue infections, and may also cause life-threatening pneumonia and bacteremia as well as serious complications including endocarditis, septic arthritis, osteomyelitis, etc. The exotoxin of *Staphylococcus aureus* may also cause food poisoning, epidermolysis bullosa and toxic shock syndrome.

Infection with *Staphylococcus aureus* is usually treated with erythromycin, penicillin, gentamicin, vancomycin or cephalothin VI. However, due to the misuse of antibiotics, a variety of new antibiotic-resistant strains emerge, and especially the rapid spread of methicillin-resistant *S. aureus* (MRSA) has made the treatment of related diseases caused by *Staphylococcus aureus* with antibiotics alone increasingly unreliable. The infection caused by the MRSA is difficult to cure with antibiotic therapy and has a high fatality rate. Therefore, the researches on *Staphylococcus aureus* vaccines and immunotherapies have been conducted widely.

The *Staphylococcus aureus* vaccines include inactivated bacterial whole-cell vaccines, genetically engineered vaccines, subunit vaccines, DNA vaccines, etc. The existing preparation methods for the *Staphylococcus aureus* vaccines include: 1) extracting one or more components of *Staphylococcus aureus* as antigens to prepare, mainly using prokaryotic expression of one or more antigens of *Staphylococcus aureus* and adsorbing the one or more antigens by an adjuvant to prepare into vaccines; 2) extracting and purifying capsular polysaccharides of *Staphylococcus aureus*, and adding one or more expressed antigen proteins of *Staphylococcus aureus* or other exogenous carrier proteins to improve the immunogenicity; 3) expressing and purifying one or more exotoxins secreted by *Staphylococcus aureus* as antigens, and combining with carrier proteins to enhance the immunogenicity; and 4) inserting coding sequences of antigenic determinants of one or more proteins of *Staphylococcus aureus* into plasmids to construct *Staphylococcus aureus* DNA vaccines. The immunogenicity of the vaccines prepared by the methods listed above is not as good as that of the bacterial whole-cell vaccines, and most of toxic proteins, conserved antigens, protective antigens and capsular polysaccharides are not covered, so there are problems such as insufficient coverage and a narrow scope of application. The inactivated bacterial whole-cell vaccines can overcome these problems and stimulate organisms to produce a large amount of immune globulins. Therefore, it is urgent to investigate a *Staphylococcus aureus* vaccine with improved immunogenicity and coverage and a wider scope of application, which can supplement and compensate for the shortcomings of the prior art.

SUMMARY

In view of this, an objective of the present invention is to provide an industrial production method for a *Staphylococcus aureus* vaccine and use of the vaccine.

An industrial production method for a *Staphylococcus aureus* vaccine, comprising the following steps:

S1 culturing a *Staphylococcus aureus* strain with an appropriate medium, to prepare into a seed liquid;

S2 inoculating the seed liquid into a fermentation tank to perform fermentation;

S3 monitoring bacterial concentration of a bacterial solution in the fermentation tank, harvesting the bacterial solution in the fermentation tank when growth of bacterial cells in the fermentation tank reaches a logarithmic phase, directly centrifuging the bacterial solution with a centrifugal force of 2000-4000×g, and collecting the bacterial cells after 10-30 min;

S4 resuspending the bacterial cells with an isotonic injection and performing concentration adjustment, and then performing irradiation using irradiation rays to cause the bacterial cells to lose proliferative activity, wherein the irradiation rays include X rays; and S5 adjusting a concentration of bacterial solution after the irradiation with the isotonic injection to $0.5\text{-}1\times10^{8}$ bacteria/ml, to obtain the *Staphylococcus aureus* vaccine.

Further, S1 comprises the following steps:

a. inoculating the *Staphylococcus aureus* strain onto a TSA plate and culturing, to obtain a primary seed; and b. inoculating the primary seed into a TSB medium to perform culture expansion two or more times, wherein the culture expansion is performed not less than twice, a concentration of inoculated bacteria at each culture expansion is 0.01-0.1 OD/ml, an inoculated volume does not exceed 10% of a culture volume, and a final concentration of the seed liquid at each culture expansion is 0.8±0.2 OD/ml.

Further, specific operation of the S1 comprises the following steps: a. inoculating the *Staphylococcus aureus* strain onto a TSA plate and culturing, to obtain a primary seed; b. inoculating the primary seed into a TSB medium, adjusting bacterial concentration to 0.01-0.1 OD/ml, and then performing culture expansion until bacterial growth reaches a logarithmic phase, to obtain a secondary seed liquid; and c. inoculating the secondary seed liquid into a fresh TSB medium, adjusting bacterial concentration to 0.01-0.1 OD/ml, and continuing culture expansion until the bacterial growth reaches the logarithmic phase, to obtain a tertiary seed liquid. In actual operation, the expanded volume in each step can be adjusted according to expansion requirements in the final process (for example, theoretically from 100 ml to 1000 ml, from 1000 ml to 10 L). From the recovery (the primary seed) of a bacterial strain (working seed) to inoculation into a fermentation tank, two expansions (that is, the secondary seed liquid, the tertiary seed liquid) are required. The reason is that the bacteria can be fully activated, the growth rate is faster and the culture time is shortened through the two expansions. Too many expansions will increase the pollution risk, and only one expansion will result in longer culture time or insufficient yield of the bacterial cells (insufficient scalability).

Further, the *Staphylococcus aureus* strain includes one or more of ATCC25923, ATCC33591, SCPH-18 and SCPH-25.

Further, a concentration of bacteria in the seed liquid inoculated in S2 is 0.01-0.1 OD/ml. The fermentation tank is arranged to contain 1 L-20 L of a fermentation broth; and in actual operation, the volume of the fermentation broth constitutes ⅓-½ of the total volume of the fermentation tank. Preferably, a 10 L fermentation tank is selected for fermentation.

Further, fermentation parameters are as follows: a ventilation volume of 3-5 L/min, a speed of 200-300 rpm, a temperature of 35-39° C., online monitoring of a pH value and a dissolved oxygen value, and culturing the bacterial cells until the logarithmic phase (1.5±0.3 OD/ml).

Further, in S3, a supernatant is discarded after centrifugation is completed, to collect the bacterial cells.

Further, in S4, the bacterial cells are resuspended with an isotonic injection and the concentration is adjusted to 0.5-$1\times10^{10}$ CFU/ml, wherein the isotonic injection includes normal saline, etc.

Further, a dose rate of the irradiation by irradiation rays is about 5-20 Gy/min, and a total dose thereof is about 2000-3000 Gy.

Further, the bacterial solution after the irradiation comprises whole bacterial cells, nucleic acids, bacterial cell fragments and membrane vesicles.

A *Staphylococcus aureus* vaccine prepared by any of the above industrial production methods.

Further, the vaccine is a whole-cell *Staphylococcus aureus* vaccine.

Further, the vaccine also comprises an adjuvant.

Further, the adjuvant includes one or more of an aluminum adjuvant, MF59, AS01, AS04, CpG and ISA51. The *Staphylococcus aureus* vaccine according to the present invention may be prepared into a type without the adjuvant, or a type with the adjuvant as required.

Further, a dosage form of the vaccine is one or more of a subcutaneous injection preparation, an intramuscular injection preparation, an oral preparation and a nasal inhalation preparation.

Further, when compared with the *Staphylococcus aureus* vaccine prepared from *Staphylococcus aureus* without the irradiation by irradiation rays, an extracellular nucleic acid of the *Staphylococcus aureus* vaccine prepared by the present invention is increased by about 20%. When compared with the extracellular nucleic acid at the completion of irradiation, the extracellular nucleic acid of the *Staphylococcus aureus* vaccine prepared by the present invention after storage at 2-8° C. for 4 weeks can be increased by 5-15 times.

Use of any of the above *Staphylococcus aureus* vaccine in preparation of a medicament for preventing or treating bacteremia caused by *Staphylococcus aureus*.

Further, an immunization procedure of the *Staphylococcus aureus* vaccine includes: subcutaneous inoculation, three injections, and an interval of two weeks for each injection.

Further, whole-cell *Staphylococcus aureus* comprised in the *Staphylococcus aureus* vaccine is $1\times10^{7}$ cells/injection-$2\times10^{7}$ cells/injection.

Use of any of the above *Staphylococcus aureus* vaccine in preparation of a medicament for preventing or treating pneumonia caused by *Staphylococcus aureus*.

Further, an immunization procedure of the *Staphylococcus aureus* vaccine includes: subcutaneous inoculation, three injections, and an interval of two weeks for each injection.

Further, whole-cell *Staphylococcus aureus* comprised in the *Staphylococcus aureus* vaccine is $1\times10^{7}$ cells/injection-$2\times10^{7}$ cells/injection.

When compared with the prior art, the present invention has the following beneficial effects:

(1) The present invention uses X rays for inactivation, and X rays will not cause obvious damage to a bacterial cell structure of *Staphylococcus aureus* (that is, X rays inactivate *Staphylococcus aureus* while maintaining the integrity of the bacterial cell structure (antigen)), to ensure that the whole-cell *Staphylococcus aureus* becomes a more effective antigen in immunization. In addition, X rays can also induce increased release of nucleic acids of *Staphylococcus aureus* (that is, an increased extracellular nucleic acid level of *Staphylococcus aureus*), and improve the immunogenicity of the vaccine. Moreover, due to the induction of X rays on the release of nucleic acids of *Staphylococcus aureus*, even if the X ray irradiation is stopped, the irradiated *Staphylococcus aureus* can still release nucleic acids continuously over time. Besides, X rays are also conducive to inducing increased release of membrane vesicles of *Staphylococcus aureus*, and further improve the immunogenicity of the vaccine.

(2) The irradiation method used in the present invention is intermittent irradiation, that is, long-term intermittent irradiation (preferably an interval of 5-10 min between the irradiations) with a dose rate of 5-20 Gy/min, which reduces the total dose of the irradiation by irradiation rays (≤3000 Gy), thereby avoiding the damage of large doses of irradiation rays on the bacterial cells and improving the immune efficacy and safety of the vaccine.

(3) The present invention provides a method for industrial production of a *Staphylococcus aureus* vaccine, to industrially produce a vaccine comprising multiple immunogenic components such as whole-cell *Staphylococcus aureus* with stable and controllable quality. In particular, the method of the present invention improves the industrial production efficiency while ensuring the retention of immunogenic substances (such as bacterial cells, bacterial cell fragments, membrane vesicles and nucleic acids) and the removal of harmful substances (such as exotoxins) and improving the efficacy and safety of the vaccine. The bacterial cell fragments are obtained by centrifugation, etc.

(4) The vaccine prepared by the present invention has good immunogenicity, not only an actual inoculated dose is low, but also the vaccine can prevent multiple infectious diseases caused by drug-resistant *Staphylococcus aureus*, such as *Staphylococcus aureus* bacteremia and *Staphylococcus aureus* pneumonia. Moreover, the vaccine prepared by the present invention may generally not comprise an adjuvant (that is, no adjuvant is required to enhance immune response of organisms), and may also be combined with an adjuvant in some scenarios (for example, the *Staphylococcus aureus* vaccine with high immunogenicity needs to be prepared). The above good immunogenicity (the protective efficacy of the vaccine) is achieved not only by the above production method, but also by the actual immunization procedure of the vaccine: reducing the total times of inoculation while extending an immunization interval. The present invention finds that the immunization procedure is conducive to improving the actual efficacy of the vaccine and extending the immunization interval is more in line with immune response rules of organisms to the vaccine.

(5) The technical solution of the present invention uses X rays for inactivation. When compared with traditional inactivation with formaldehyde and thermal inactivation, a release level of nucleic acids is increased and there is no chemical residue, which improves the immunogenicity of the vaccine, while avoiding the risk of allergic reactions and carcinogenicity caused by chemical inactivators to some extent, improving the safety of the vaccine and reducing side effects.

DESCRIPTION OF DRAWINGS

To make the embodiments of the present invention or the technical solutions in the prior art clearer, the drawings required to be used in the description of the embodiments or the prior art will be briefly introduced below. It is obvious that the drawings described below are some embodiments of the present invention, and that other drawings can be obtained from these drawings for those of ordinary skill in the art without making inventive effort.

DETAILED DESCRIPTION

Figure 1:
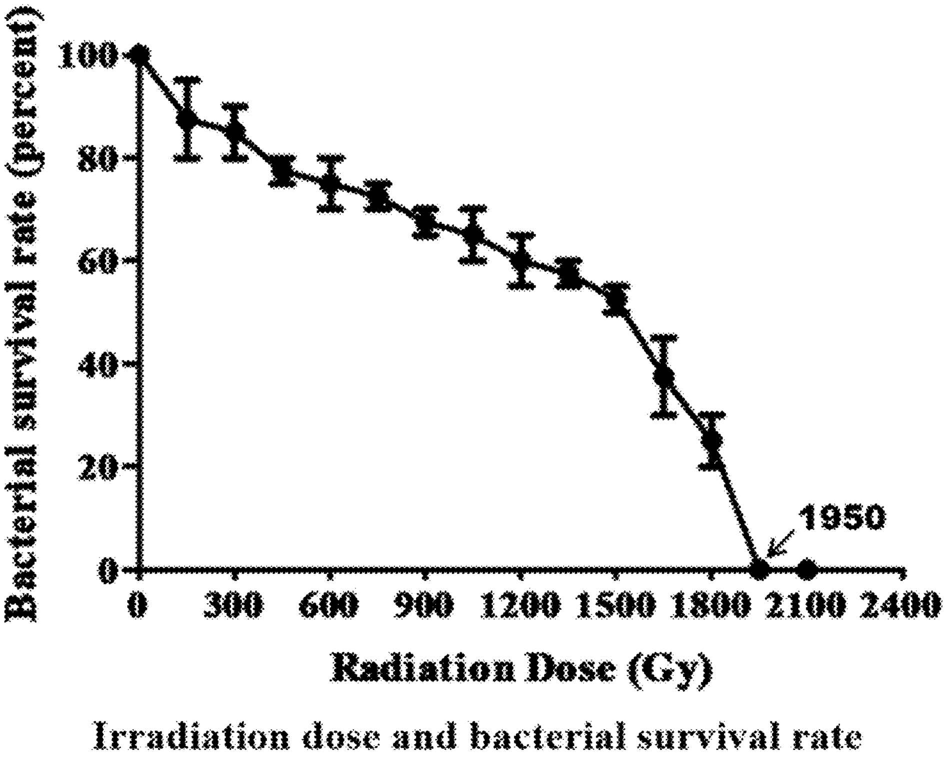
FIG. 1 is a diagram showing irradiation (radiation) dose and bacterial survival rate.

To make the objective, the technical solutions and advantages of the embodiments of the present invention clearer, the technical solutions of the embodiments of the present invention will be clearly and completely described below in combination with drawings. It is obvious that the described embodiments are some of the embodiments of the present invention, not all of the embodiments. Based on the embodiments of the present invention, all other embodiments obtained by those of ordinary skill in the art without making inventive effort shall belong to the protection scope of the present invention.

It should be noted that the term "include", "comprise" or any variant thereof is intended to encompass nonexclusive inclusion so that a process, method, article or device including a series of elements includes not only those elements but also other elements which have been not listed definitely or an element(s) inherent to the process, method, article or device. Moreover, the expression "comprising a (n) . . . " in which an element is defined will not preclude presence of an additional identical element(s) in a process, method, article or device comprising the defined element(s) unless further defined.

As used herein, the term "about", typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Embodiment 1

Preparation method for a *Staphylococcus aureus* vaccine

1. Media and Reagents

Tryptic Soy Broth (TSB)

Tryptic Soy Agar (TSA)

Sodium chloride injection (0.9%)

2. Vaccine Preparation Process

1) Preparation of a Primary Seed

Glycerol stocks of bacterial strains were taken out of a −80° C. ultra-low temperature freezer, streaked and inoculated on a TSA plate and cultured for 16±1 h at 37±1° C. In the present embodiment, the bacterial strains used were ATCC25923.

2) Preparation of a Secondary Seed Liquid

An appropriate amount of bacterial cells were scraped in 10 ml of the TSB, and a concentration of bacterial solution was measured with a spectrophotometer. An appropriate volume of the bacterial solution was inoculated into 100 ml of the TSB to a final concentration of about 0.05 OD/ml, and subjected to shaking culture at 37±1° C. and 220 rpm until 0.8±0.2 OD/ml (a logarithmic phase).

3) Preparation of a Tertiary Seed Liquid

The secondary seed liquid was taken, and a concentration of bacterial solution was measured with a spectrophotometer. An appropriate volume of the bacterial solution was inoculated into 1000 ml of the TSB to a final concentration of about 0.05 OD/ml, and subjected to shaking culture at 37±1° C. and 220 rpm until 0.8±0.2 OD/ml (a logarithmic phase).

4) Culture in a Fermentation Tank

The tertiary seed liquid was taken, and a concentration of bacterial solution was measured with a spectrophotometer. An appropriate volume of the bacterial solution was inoculated into 4 L of the TSB to a final concentration of about 0.05 OD/ml. The fermentation parameters were set as follows: a ventilation volume of 3-5 L/min, a speed of 250±20 rpm, a temperature of 37±1° C. for culture, online pH and dissolved oxygen monitoring, culturing to 1.5±0.3 OD/ml (a logarithmic phase).

5) Harvesting of the Bacterial Cells

The bacterial solution was loaded into a centrifuge barrel and centrifuged for 20 min at 3000×g at room temperature. The bacterial cells were resuspended with 20 ml of the sodium chloride injection (0.9%), subjected to washing by centrifugation once and resuspended with 20 ml of the sodium chloride injection (0.9%).

6) Adjustment of the Concentration

The concentration of bacterial solution was adjusted to $0.5\text{-}1\times10^{10}$ CFU/ml.

7) Inactivation with X Rays

The bacterial solution was subpackaged in sealable containers (such as 50 ml centrifuge tubes) with a liquid level not exceeding 1 cm. When the total dose of the irradiation rays was greater than or equal to 2000 Gy, the bacterial solution could be completely inactivated. From the perspective of complete inactivation of the bacterial solution and not too large total dose (too large total dose would cause whole bacterial cells to rupture and release bacterial toxins), the total dose for inactivation was determined to be 2000-3000 Gy. It was appropriate to set the dose rate to 5-20 Gy/min. When the dose rate was too low (i.e., <5 Gy/min), the total irradiation time (>400 min) and the total production time would be extended (>8 h), and the bacterial solution also had a risk of degradation and exposure to pollution due to long-term exposure to an ambient temperature and a production environment in addition to affecting the production efficiency. When the dose rate was too high (i.e. >20 Gy/min), the total irradiation time (<100 min) was too short, the sufficient total irradiation time (≥2 h) could not be guaranteed, which still negatively affected the degree of inactivation. The detailed inactivation parameters are affected by many factors such as the performance of irradiation equipment, a shape of a container loading the bacterial solution, liquid level and concentration of bacterial solution. Therefore, the dose rate, the total dose, the irradiation times and the interval between irradiations can be adjusted according to the actual production needs. Preferably, the interval between irradiations is 5-10 min.

8) Raw Liquid

After the irradiation, 1/100 of the volume of the bacterial solution was taken, coated on the TSA plate, and cultured for 48 h at 37±1° C., to determine that there were no bacteria growing. At the same time, 1/100 of the volume of the bacterial solution was taken for the sterility test according to Chinese Pharmacopoeia (General Rule 1101).

9) Finished Vaccine

A bacterial cell concentration of the vaccine was adjusted to $0.5\text{-}1\times10^{8}$ bacteria/ml with the sodium chloride injection (0.9%), that is, the finished vaccine. The finished vaccine was stored at 2-8° C. It needs to be noted that the concentration of viable bacterial cells is expressed in colony-forming units of bacteria per milliliter "CFU/ml"; the concentration of inactivated bacterial cells is expressed in the number of bacteria per milliliter "bacteria/ml". As used herein, "1 CFU/ml" is considered equivalent to the bacterial cell concentration indicated by "1 bacterium/ml".

Embodiment 2

Investigation on the Inactivation Dose

In the present embodiment, X rays were used to inactivate *Staphylococcus aureus* strains.

Method: before irradiation, the prepared bacterial solution was diluted, spread on a plate and counted. After each irradiation, the bacterial solution was sampled, diluted, spread on a plate and counted. 3 copies were taken for each sampling and counted, respectively, and the bacterial survival rate was calculated after each irradiation.

Calculation formula of the bacterial survival $$\text{rate} = \frac{\text{bacterial concentration after irradiation}}{\text{bacterial concentration before irradiation}} \times 100\%.$$

Results: X rays have a unique bactericidal mechanism, that is, inducing DNA damage to inactivate the bacteria. As shown in FIG. 1, the inactivation dose of X rays for the *Staphylococcus aureus* ATCC25923 is greater than or equal to 1950 Gy. However, considering that it needs to be guaranteed that the bacterial solution is completely inactivated during actual production, the inactivation dose can be set to be greater than or equal to 2000 Gy, and even the inactivation dose is extended to 2100 Gy by one dose point.

Embodiment 3

Investigation on effects of different inactivation methods on nucleic acid release levels of the vaccine Method:

1. A batch of bacterial solution was prepared at the same batch, divided into 5 parts on average and treated as follows.
2. Viable bacteria for control: the viable bacteria were placed at room temperature without any treatment;
3. Half-inactivation dose: treating according to an inactivation procedure of X rays, with a total dose of 1050 Gy;
4. Inactivation dose: treating according to an inactivation procedure of X rays, with a total dose of 2100 Gy;
5. Inactivation with formaldehyde: performing inactivation treatment for 24 h at 37±1° C. by adding a formaldehyde solution until a final concentration of 1%, and changing the solution and washing with the sodium chloride injection (0.9%) for 3-5 times after the inactivation;
6. Thermal inactivation: autoclaving for 15 min at 121° C.;
7. Nucleic acid release determination: after all samples were inactivated, the samples were taken immediately (0 week) for centrifugation. A supernatant was taken, and a nucleic acid concentration was determined with an ultraviolet spectrophotometer (A260). Samples were taken again for determination after 2 or 4 weeks.

Figure 2:
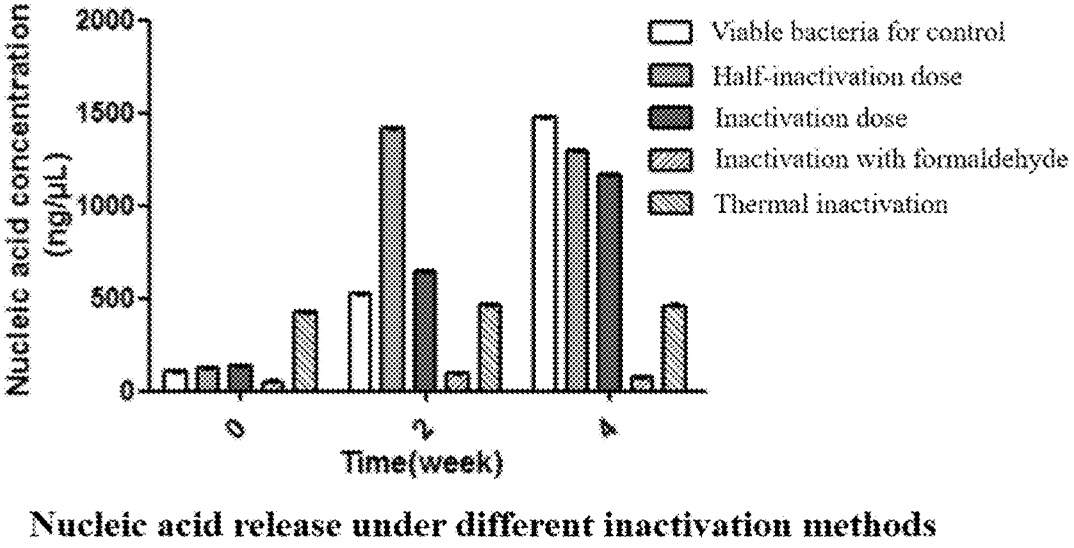
FIG. 2 is a diagram showing nucleic acid release under different inactivation methods.

Results: as shown in FIG. 2, the X-ray inactivation induces an increase in the extracellular nucleic acid level of *Staphylococcus aureus*, and the process of nucleic acid release continues over time. The nucleic acid release is one of the important features that distinguish the X-ray inactivation from the inactivation with formaldehyde and thermal inactivation, which may bring more immunogenicity to the vaccine and activate more immune signaling pathways such as STING and TLR9.

The activation of the STING pathway facilitates the recognition of bacterial infection by an immune system, the production of type I interferon (enhancing cellular immunity), the presentation of vaccine antigen components and the recognition by the immune system in an immune stage, and the removal of bacteria in an infective stage. The TLR9 pathway is a main receptor for recognizing bacterial CpG DNA in the immune system, thereby inducing the production of a series of proinflammatory cytokines and chemokines, and finally causing Th1-like inflammatory reactions. Bacterial vaccines mainly induce humoral immunity, and the cellular immunity induced by them is weaker. Both STING and TLR9 pathways activated by bacterial nucleic acids are conducive to enhancing Th1 cellular immunity and improving immune effects.

Embodiment 4

Electron Microscopy Observation of the Bacterial Cells after X-Ray Inactivation

Preparation Method of Samples for a Scanning Electron Microscope:

1. Sample preparation: according to a preparation process of the *Staphylococcus aureus* vaccine, after *Staphylococcus aureus* was inactivated, a raw liquid was taken for preparing the samples for the scanning electron microscope.
2. Fixation: 200 μl of the inactivated vaccine raw liquid was taken and centrifuged for 10 min at 3000×g, a supernatant was discarded, and 1 ml of 2%-3% glutaraldehyde was added for fixing overnight at 4° C.
3. Washing: washing for 3 times with 0.1 M PBS.
4. Dehydration: after that, dehydrating once with 30%, 50%, 70%, 80%, 90% of ethanol successively, and dehydrating for 3 times with 100% absolute ethanol (blowing away the bacterial cells as gently as possible at each dehydration). Treating for 10 min each time, and centrifuging for 5 min at 3000×g.

5. Drying: drying for 1 h at 35° C. with $CO_2$ critical-point drying method.
6. Adhesion and coating: the samples were pasted onto a metal sample holder with a special double-sided tape, and a layer of gold film was coated on the samples by ion sputtering.
7. Scanning imaging.

Figure 3:
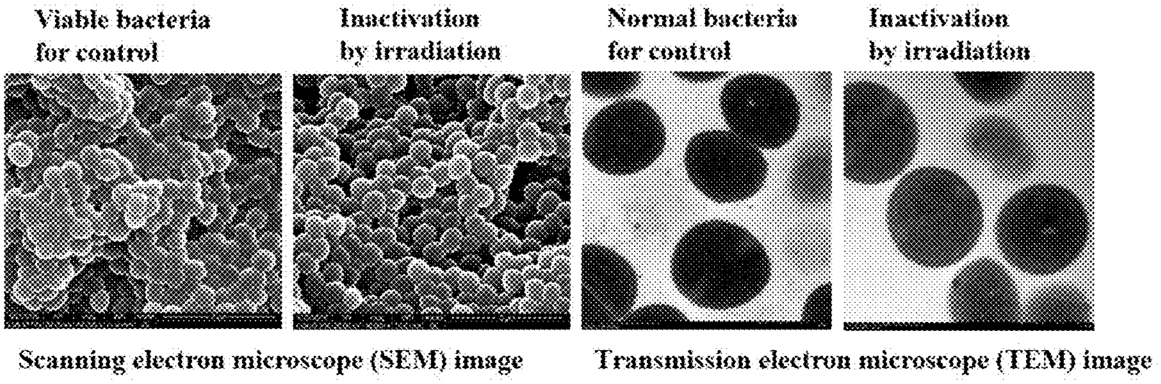
FIG. 3 is a scanning electron microscope (SEM) image and a transmission electron microscope (TEM) image of the inactivated bacterial cells.

Results: as shown in scanning electron microscope results in FIG. 3, the X-ray inactivation does not cause obvious damage to a bacterial cell structure of *Staphylococcus aureus*, that is, X rays inactivate *Staphylococcus aureus* while maintaining the integrity of the bacterial cell structure (antigen), so that *Staphylococcus aureus* may become a more effective antigen in immunization.

Preparation Method of Samples for a Transmission Electron Microscope:

1. Sample preparation: according to a preparation process of the *Staphylococcus aureus* vaccine, after *Staphylococcus aureus* was inactivated, a raw liquid was taken for preparing the samples for the transmission electron microscope.
2. Pre-fixation: 200 μl of the inactivated vaccine raw liquid was taken and centrifuged for 10 min at 3000×g, a supernatant was discarded, and 1 ml of 2%-3% glutaraldehyde was added for fixing overnight at 4° C.
3. Washing: washing for 3 times with 0.1 M PBS.
4. Post-fixation: fixing for 2 h with 1% osmic acid fixation liquid.
5. Washing: washing for 3 times with 0.1 M PBS.
6. Dehydration: after that, dehydrating once with 30%, 50%, 70%, 80%, 90% of acetone successively, and dehydrating for 3 times with 100% pure acetone (blowing away the bacterial cells as gently as possible at each dehydration). Treating for 30 min each time, and centrifuging for 5 min at 3000×g.
7. Permeation: pure acetone+embedding liquid (1:2) overnight at room temperature.
8. Embedding: the permeated samples were picked into an embedding plate, 37° C. overnight, 45° C. for 12 h, 60° C. for 48 h.
9. Ultrathin section.
10. Negative staining: dripping one drop of 1% phosphotungstic acid to perform staining for 1-2 min, and absorbing a staining solution with filter paper. Dripping one drop of pure water, absorbing with filter paper, repeating the foregoing steps for two or three times to wash excess phosphotungstic acid, and standing to dry.
11. Imaging by the transmission electron microscope.

Results: as shown in transmission electron microscope results in FIG. 3, X rays inactivate *Staphylococcus aureus* while maintaining the integrity of the bacterial cell structure (antigen).

Embodiment 5

Investigation on the protective efficacy of the *Staphylococcus aureus* vaccine in a model of *Staphylococcus aureus* bacteremia (bloodstream infection)

Method:

1. Test groups: in the test, four strains of *Staphylococcus aureus* were selected to challenge a vaccine-immunized group, respectively, including Methicillin Sensitive *Staphylococcus aureus* (MSSA) ATCC25923, Methicillin-resistant *Staphylococcus aureus* (MRSA) ATCC33591, and two strains of clinically isolated multi-drug resistant (MDR) *Staphylococcus aureus* SCPH-18 and SCPH-25. 10 mice for an unimmunized group and 10 mice for an immunized group, respectively.
2. Immunization: the finished vaccine (0.5-1×$10^8$ bacteria/ml) was taken to immunize C57BL/6 mice at 6-8 weeks of age, and 0.2 ml (1-2×$10^7$ bacteria/injection) was subcutaneously injected into groins, three injections and at an interval of 2 weeks. The challenge was carried out after two weeks since the last immunization.
3. Establishment of the bloodstream infection model 3.1 The challenge strains (ATCC25923, ATCC33591, SCPH-18, SCPH-25) were recovered on blood plates, and cultured for 16±1 h at 37±1° C.

3.2 Monoclonal strains were picked and inoculated in 3 ml of the TSB, and cultured for 16±1 h at 37±1° C.

3.3 A concentration of bacterial solution was measured with a spectrophotometer. An appropriate volume of the bacterial solution was inoculated into 20 ml of the TSB to a final concentration of about 0.05 OD/ml, and subjected to shaking culture at 37±1° C. and 220 rpm until 0.8±0.2 OD/ml (a logarithmic phase).

3.4 The bacterial solution was centrifuged for 10 min at 3000×g at room temperature, the bacterial cells were resuspended with 2 ml of the sodium chloride injection (0.9%), and the concentration of bacterial solution was adjusted to 0.5-1×$10^9$ CFU/ml.

3.5 The bacterial solution was intravenously injected at tails of the mice with 0.1 ml/mouse (0.5-1×$10^8$ CFU/mouse).

3.6 Survival rates of the mice in the immunized group and the unimmunized group within one week were observed and counted.

Figure 4:
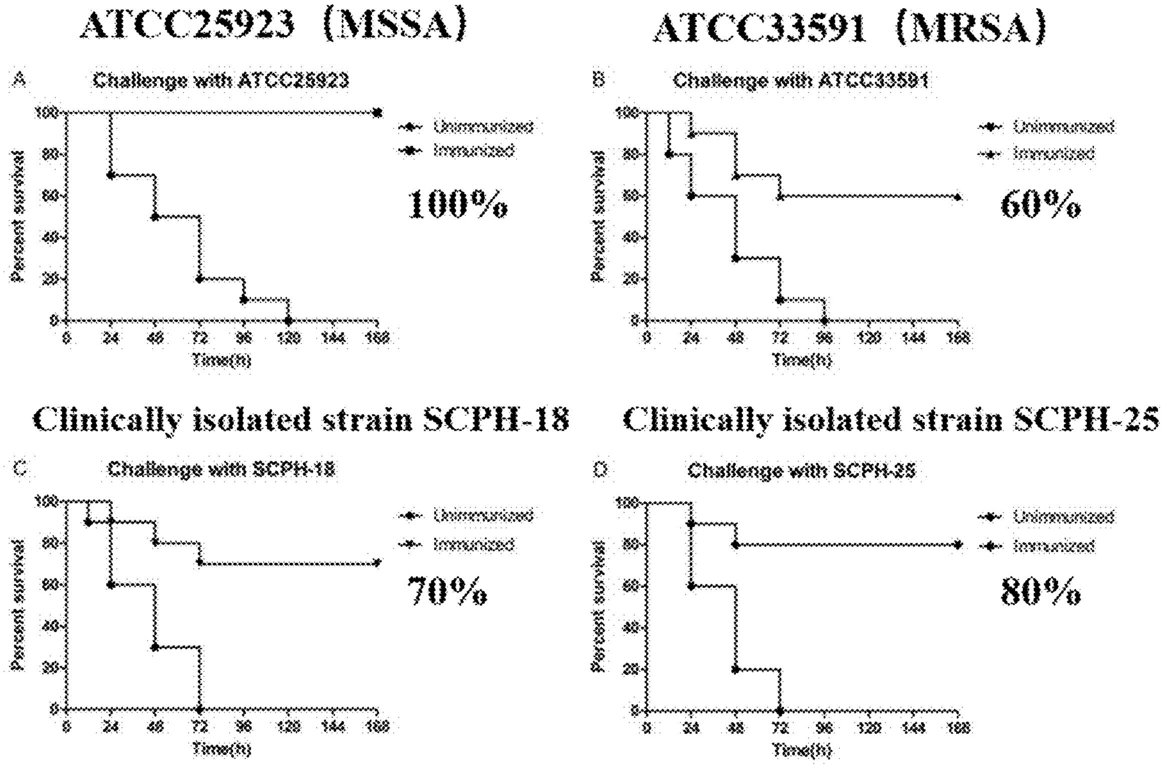
FIG. 4 is a diagram showing protective efficacy of a *Staphylococcus aureus* vaccine in a bacteremia model.

Results: as shown in FIG. 4, all mice in the unimmunized group die within 72-120 h after the challenge strains attack, and immune protective rates for the mice in the immunized group after the challenge strains attack are 100% (ATCC25923), 60% (ATCC33591), 70% (SCPH-18) and 80% (SCPH-25), respectively, that is, the protective rates of the *Staphylococcus aureus* vaccine against the *Staphylococcus aureus* bacteremia are 60% and above.

Embodiment 6

Investigation on the protective efficacy of the *Staphylococcus aureus* vaccine in a model of *Staphylococcus aureus* pneumonia (airway infection)

Method:

1. Test groups: in the test, four strains of *Staphylococcus aureus* were selected to challenge a vaccine-immunized group, respectively, including Methicillin Sensitive *Staphylococcus aureus* (MSSA) ATCC25923, Methicillin-resistant *Staphylococcus aureus* (MRSA) ATCC33591, and two strains of clinically isolated multi-drug resistant (MDR) *Staphylococcus aureus* SCPH-18 and SCPH-25. 35 mice for an unimmunized group and 35 mice for an immunized group, respectively, and 3-5 mice per time point.
2. Immunization: the finished vaccine (0.5-1×$10^8$ bacteria/ml) was taken to immunize C57BL/6 mice at 6-8 weeks of age, and 0.2 ml (1-2×$10^7$ bacteria/injection) was subcutaneously injected into groins, three injections and at an interval of 2 weeks. The challenge was carried out after two weeks since the last immunization.
3. Establishment of the pneumonia (airway infection) model 3.1 The challenge strains (ATCC25923, ATCC33591, SCPH-18, SCPH-25) were recovered on blood plates, and cultured for 16±1 h at 37±1° C.

3.2 Monoclonal strains were picked and inoculated in 3 ml of the TSB, and cultured for 16±1 h at 37±1° C.

3.3 A concentration of bacterial solution was measured with a spectrophotometer. An appropriate volume of the bacterial solution was inoculated into 20 ml of the TSB to a final concentration of about 0.05 OD/ml, and subjected to shaking culture at 37±1° C. and 220 rpm until 0.8±0.2 OD/ml (a logarithmic phase).

3.4 The bacterial solution was centrifuged for 10 min at 3000×g at room temperature, the bacterial cells were resuspended with 2 ml of the sodium chloride injection (0.9%), and the concentration of bacterial solution was adjusted to 2-4×$10^8$ CFU/ml.

3.5 The bacterial solution was injected into the mice through airways with 0.05 ml/mouse (1-2×$10^7$ CFU/mouse).

3.6 The bacterial load in lungs of the mice in the immunized group and the unimmunized group within one week was observed and counted.

Figure 5:
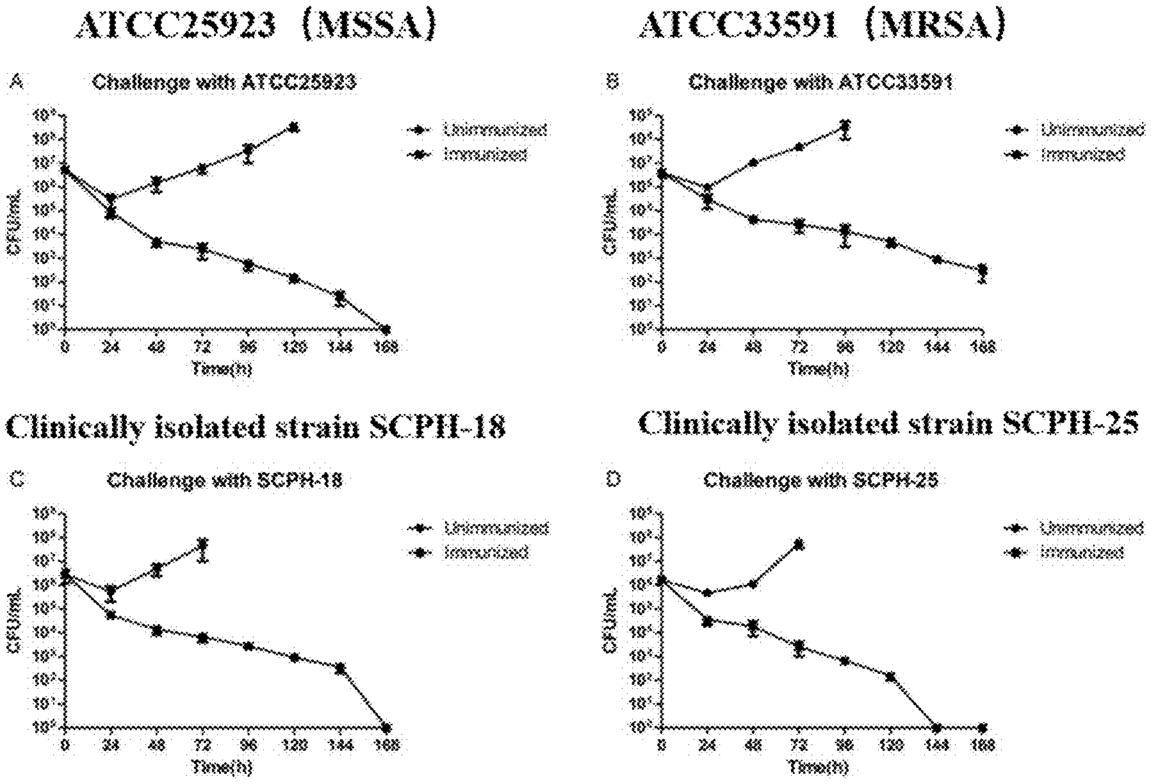
FIG. 5 is a diagram showing protective efficacy of a *Staphylococcus aureus* vaccine in a pneumonia model.

Results: as shown in FIG. 5, after the challenge strains attack, the bacterial load in lungs of the mice in the unimmunized group shows a significant growth trend, and all mice in the unimmunized group die within 72-120 h; the immunized group shows a clear removal trend for the challenge strains, or even complete removal.

The embodiments of the present invention are described above with reference to the accompanying drawings, but the present invention is not limited to the aforementioned specific embodiments. The aforementioned embodiments are merely illustrative and not limiting. For those of ordinary skill in the art, many forms can be made under the teaching of present invention without departing from the spirit of the present invention and the scope of the claims, all of which shall fall within the protection scope of the present invention.

The invention claimed is:

1. An industrial method of producing a vaccine comprising X-ray irradiated *Staphylococcus aureus*, the method comprising the following steps:

(a) culturing *Staphylococcus aureus* bacteria of the ATCC 25923 strain on a tryptic soy agar (TSA) plate and then culturing in a tryptic soy broth (TSB) medium to obtain a primary seed, (b) inoculating the primary seed of step (a) into a TSB medium, adjusting the concentration to 0.01-0.1 optical density (OD) per ml and then performing culture expansion until the growth of the *Staphylococcus aureus* bacteria reaches logarithmic phase to obtain a secondary seed liquid, (c) inoculating the secondary seed liquid into a fresh TSB medium, adjusting the concentration to 0.01-0.1 OD per ml and performing culture expansion until the growth of the *Staphylococcus aureus* bacteria from the secondary seed liquid of step (b) reaches logarithmic phase to obtain a tertiary seed liquid, wherein final concentration of the seed liquid at each of the culture expansions is 0.8±0.2 OD/ml, (d) inoculating the tertiary seed liquid of step (c) into a fermentation tank containing a volume of TSB fermentation broth that is ⅓ to ½ of the total volume of the fermentation tank to produce a solution of the *Staphylococcus aureus* bacteria, (e) monitoring the concentration of the solution of the *Staphylococcus aureus* bacteria in the fermentation tank of step (d), (f) harvesting the solution from step (e) when the growth of the *Staphylococcus aureus* bacteria reaches logarithmic phase followed by directly centrifuging the solution with a centrifugal force of 2000 to 4000×g and collecting the centrifuged the *Staphylococcus aureus* bacteria after 10-30 minutes, (g) resuspending the *Staphylococcus aureus* bacteria collected in step (f) by isotonic injection and adjusting the concentration to 0.5-1×$10^{10}$ of the bacteria per ml and then (h) performing intermittent X-ray irradiation of the resuspended *Staphylococcus aureus* bacteria at an irradiation dose rate of 5-20 Gy/minute for a total inactivating irradiation dose of 2000-3000 Gy with an interval of 5-10 minutes between the irradiations to cause the cells of the *Staphylococcus aureus* bacteria to lose their proliferative activity; and (i) adjusting the concentration of the X-ray irradiated *Staphylococcus aureus* bacteria to 0.5-1×$10^8$ per ml to obtain the X-ray irradiated *Staphylococcus aureus* vaccine, wherein the vaccine comprises whole cells and cell fragments, nucleic acids, and membrane vesicles of the *Staphylococcus aureus* strain released by the X-ray irradiation and wherein the vaccine has the capacity to confer protection against *Staphylococcus aureus* airway infection as determined in a mouse model of *Staphylococcus aureus* pneumonia or against *Staphylococcus aureus* blood infection as determined in a mouse model of *Staphylococcus aureus* bloodstream infection upon subcutaneous immunization of mice with 1 to 2×$10^7$ of the bacteria per ml dose of the X-ray irradiated *Staphylococcus aureus* vaccine.

2. The X-ray irradiated *Staphylococcus aureus* vaccine produced by the method of claim 1.

3. A method of immunization of mice, the method comprising three subcutaneous injections of the X-ray irradiated *Staphylococcus aureus* vaccine produced by the method of claim 1 to the mice comprising 1 to 2×$10^7$ of the bacteria per ml of the X-ray irradiated *Staphylococcus aureus* vaccine.

4. The method of claim 3, wherein the immunization comprises three subcutaneous injections of the vaccine with an interval of two weeks between the injections.

* * * * *